United States Patent
Graser et al.

[11] Patent Number: 5,820,739
[45] Date of Patent: Oct. 13, 1998

[54] MEASURING INSTRUMENT

[75] Inventors: Theodor Graser; Gerhard Hoetzel; Johann Wehrmann, all of Stuttgart; Heinz Eisenschmid, Wettstetten, all of Germany

[73] Assignee: Robert Bosch GmbH, Stuttgart, Germany

[21] Appl. No.: 737,130

[22] PCT Filed: Mar. 19, 1996

[86] PCT No.: PCT/DE96/00484

§ 371 Date: Nov. 15, 1996

§ 102(e) Date: Nov. 15, 1996

[87] PCT Pub. No.: WO97/03483

PCT Pub. Date: Jan. 30, 1997

[30] Foreign Application Priority Data

Jul. 12, 1995 [DE] Germany .................. 195 26 821.0

[51] Int. Cl.⁶ .................................................. G01N 27/407
[52] U.S. Cl. .................. 204/421; 204/424; 204/427; 205/784.5
[58] Field of Search ............... 204/421–429; 205/784.5

[56] References Cited

U.S. PATENT DOCUMENTS

| | | | |
|---|---|---|---|
| 3,630,874 | 12/1971 | Olette et al. | 204/422 |
| 3,758,397 | 9/1973 | Rittiger et al. | 204/423 |
| 3,784,459 | 1/1974 | Jackson | 204/423 |
| 4,096,050 | 6/1978 | Kobayashi et al. | 204/428 |
| 4,116,797 | 9/1978 | Akatsuka | 204/428 |
| 4,151,503 | 4/1979 | Cermak et al. | 73/23 |
| 4,399,017 | 8/1983 | Inoue et al. | 204/425 |
| 4,452,687 | 6/1984 | Torisu et al. | 204/428 |
| 4,560,463 | 12/1985 | Frey et al. | 204/424 |
| 4,708,783 | 11/1987 | Nakamura et al. | 204/423 |
| 4,818,364 | 4/1989 | Weber et al. | 204/428 |

FOREIGN PATENT DOCUMENTS

| | | |
|---|---|---|
| 0624790 A1 | 11/1994 | European Pat. Off. . |
| 3410122 | 10/1985 | Germany . |

*Primary Examiner*—T. Tung
*Attorney, Agent, or Firm*—Spencer & Frank

[57] ABSTRACT

The invention relates to a measuring instrument, particularly an electrochemical measuring sensor, having a sensor element arranged at a measuring point, which sensor element can be connected via electrical connecting leads with an evaluating circuit removed from the measuring point, with the electrical connecting leads being guided so as to be protected against external influences, especially against high temperature influences, at least in the proximity of the measuring point. At its end facing away from the sensor element (12), a protective device (24) receiving the electrical connecting leads (22) is provided with a connecting device (30) which can be connected to a connecting lead (54, 56) to the evaluating circuit.

7 Claims, 1 Drawing Sheet

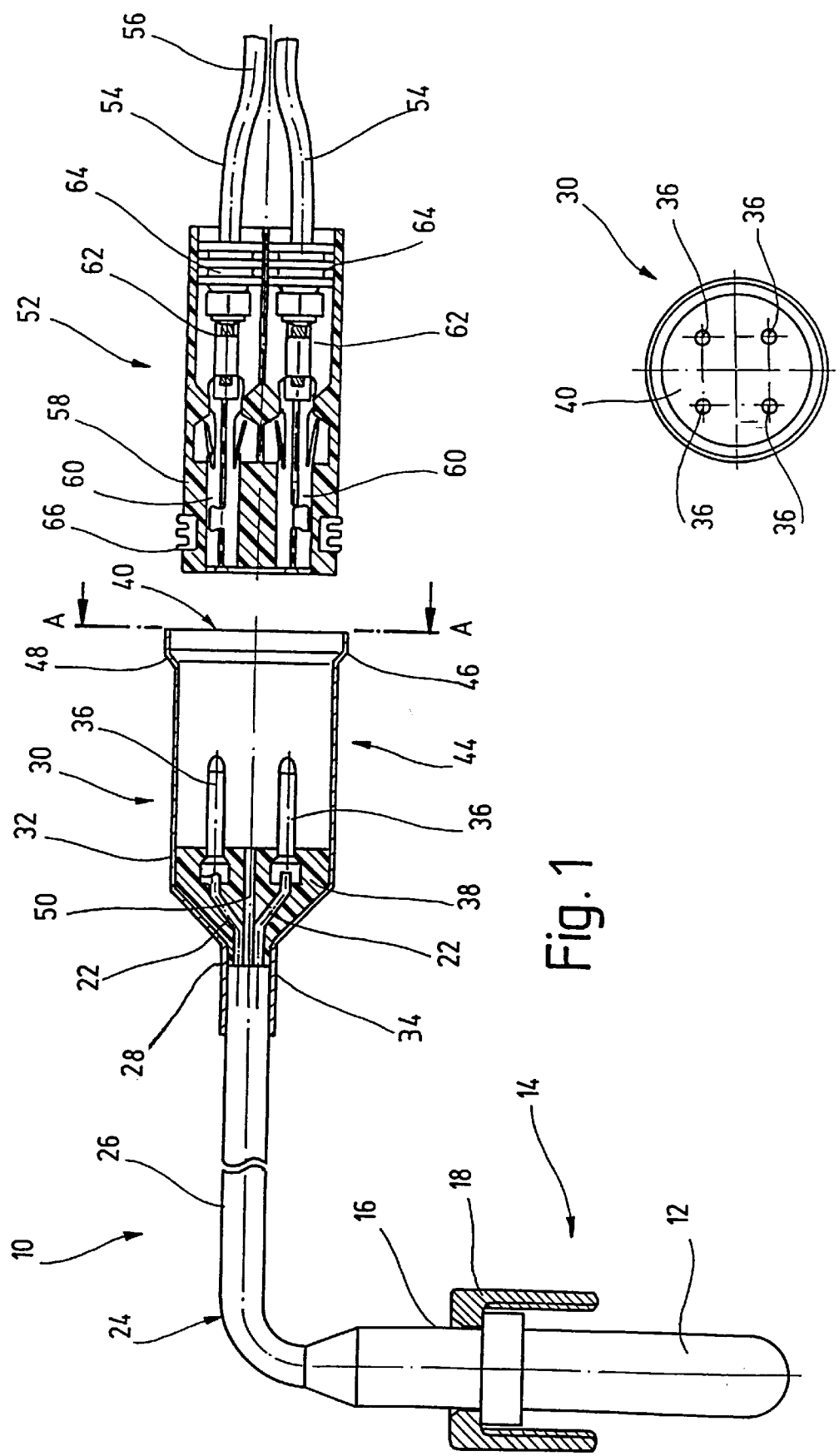

MEASURING INSTRUMENT

BACKGROUND OF THE INVENTION

The invention relates to a measuring instrument, particularly an electrochemical measuring sensor, of the type having a sensor element arranged at a measuring point, which sensor element can be connected via electrical connecting leads with an evaluating circuit removed from the measuring point, and with the electrical connecting leads being guided so as to be protected against external influences, especially against high temperature influences, at least in the proximate of the measuring point.

PRIOR ART

Measuring instruments of the generic type mentioned above are known. Electrochemical measuring sensors, for example, designed in a so-called finger construction, are used in motor vehicles to determine the oxygen content in exhaust gases of internal combustion engines. These measuring instruments have a sensor element which is arranged directly at a measuring point and which is fixed so as to be sealed in a metallic housing.

As is known, the sensor element has a solid-state electrolyte which is arranged between two electrodes. Depending on the outfitting of the sensor element, an additional heating device is provided. In order to evaluate the sensor signals determined with the sensor element or to supply the sensor element with the necessary heating voltage, electrical connecting leads are provided which connect the sensor element with a corresponding circuit arrangement.

Since the sensor elements, for example, during measuring of the oxygen content in exhaust gases, are arranged in a region which is exposed to a relatively high temperature, it is known to guide the electrical connecting leads so that they are protected at least in the proximity of the measuring instrument. For this purpose, it is known to guide the electrical connecting leads in a metal tube which ends at a specific distance from the measuring point. For realizing the connection of the sensor element with the evaluating circuit, lines insulated with plastic material, usually PTFE-insulated, are fixed to the end of the lines that are guided in the metal tube. At their other end, the lines insulated with plastic material are provided with a plug device which can be connected to a counterplug device disposed on the cable harness.

As is known, the connection between the lines insulated with plastic material and the lines disposed in the metal tube is implemented as a nondetachable welded, crimped and/or soldered connection. To ensure the operating safety of this connection point, it is known to coat it with plastic material and to additionally seal the lines insulated with plastic material with rubber bushes. The drawback of this solution is that the cable harness of the electrical connecting leads, which harness is connected to the measuring instrument, is relatively long, for example, up to two meters, so that a relatively complex installation in the motor vehicle is required.

SUMMARY AND ADVANTAGES OF THE INVENTION

The above mentioned problems according to the prior art generally are overcome according to the present invention by a measuring instrument, particularly an electrochemical measuring sensor, having a sensor element arranged at a measuring point, which sensor element can be connected via electrical connecting leads with an evaluating circuit removed from the measuring point, with the electrical connecting leads being guided so as to be protected against external influences, especially against high temperature influences, at least in the proximity of the measuring point, and wherein at its end facing away from the sensor element, a protective device receiving the electrical connecting leads is provided with a connecting device which can be connected to a connecting lead to the evaluating circuit.

In contrast, to the known device the measuring instrument according to the invention described above offers the advantage that, in a simple manner, compact, high-temperature-capable measuring instruments can be reliably connected with a connection leading to an evaluating circuit without great complexity. Since, at its end facing away from the sensor element, a protective device which receives the connecting leads is provided with a connecting device which can be connected with a connecting lead to the evaluating circuit, it is possible in an advantageous manner to implement the connection between the measuring instrument and the evaluating circuit directly at the end of the measuring instrument which is removed from the measuring point without necessitating an additional arrangement or production of an interface.

Since the measuring instrument is directly provided with the connecting device, the instrument can be built in a very compact manner, thus allowing a simplified installation, for example, in the engine compartment of a motor vehicle. Furthermore, it is possible in an advantageous manner to create a uniform interface to the connecting leads to the evaluating circuit via the connecting device which is directly connected with the measuring instrument, particularly with the protective device of the measuring instrument, so that, overall, a measuring instrument is created which can be used in a plurality of different motor vehicles.

Further advantageous embodiments of the invention result from the other characteristics listed in the dependent claims.

BRIEF DESCRIPTION OF THE DRAWINGS

In the following, the invention is explained in greater detail in an embodiment by way of the associated drawings wherein:

FIG. 1 is a schematic sectional view of a measuring instrument, according to the invention and, FIG. 2 is a plan view of a connecting device of the measuring instrument.

DETAILED DESCRIPTION OF THE PREFERRED EMBODIMENTS

FIG. 1 shows a measuring instrument, altogether identified by 10, in a partially cut illustration. The measuring instrument 10 has a sensor element 12. In principle, the sensor element 12 may be any desired sensor element for measuring a physical magnitude. In the illustrated example, it is assumed that the sensor element 12 is an electrochemical measuring sensor 14, a so-called lambda sensor. The sensor element 12 has a housing 16 which is essentially finger-shaped and which can be secured in an exhaust gas pipe, not shown. The housing 16 is guided through a through-opening of the exhaust gas pipe and is fixed in place with corresponding fixing means, for example, a union nut 18. The fastening of the housing 16 takes place such that it is arranged in the through-opening so as to be sealing.

Inside of the housing 16 are arranged, not shown here, electrodes, a solid-state electrolyte as well as a heating device; by means of all these, an oxygen concentration in an exhaust gas of a motor vehicle can be measured in a manner which does not have to be considered here in detail. The electrodes and the heating device are guided out of the housing 16 of the sensor element 12 via electrical connecting leads 22. In the example, it is assumed that altogether four connecting leads 22 are provided. But according to further embodiments, which are not shown, the number of the connecting leads may vary in accordance with the outfitting of the sensor element 12, that is, the number may be greater or smaller than four.

On the one hand, the connecting leads 22 serve to pick up sensor signals and, on the other hand, to make available a heating voltage.

A protective device 24 for the connecting leads 22 adjoins the housing 16 of the sensor element 12. The protective device 24 may be, for example, a metal sheath line 26 inside of which the connecting leads 22 are guided. The metal sheath line 26 is connected to the housing 16 of the sensor element 12 so as to be sealing so that external influences, for example, dirt, fuel gases, air or heat are prevented from entering the housing 16 in an uncontrolled manner. Since the sensor element 12 is usually arranged in a region in which elevated temperatures, for example, of several 100° C. prevail, the metal sheath line 26 forms a protection for the electrical connecting leads 22 against inadmissible heating.

At the end 28 of the metal sheath line 26 that is facing away from the sensor element 12, a connecting device 30 is arranged which, together with the sensor element 12, the protective device 24 forms a constructive unit which results in the measuring instrument 10. The connecting device 30 has a housing 32 which is fixedly connected with the metal sheath line 26. For this purpose, the housing 32 forms a flange 34 through which the metal sheath line 26 is guided into the interior of the housing 32. The housing 32 may be comprised, for example, of a plastic material which is molded onto the metal sheath line 26. According to a further embodiment, the housing 32 may be a metal housing which is fixedly connected, for example, soldered or welded, to the metal sheath line 26. According to a further embodiment, not shown, the housing 32 is designed so as to be of one piece unitary construction with the metal sheath line 26, that is, the exterior metal sheath of the metal sheath line 26 widens to form the housing 32. In each case it is ensured that the housing 32 is connected with the metal sheath line 26 so as to be fixed and sealing. The connection between the housing 32 and the metal sheath line 26 is selected such that it withstands the temperatures prevailing at the connection point. Depending on the length of the metal sheath line 26, which according to different embodiments may be, for example, between five and twenty-five cm, temperatures, for example, of approximately 150° C. prevail at the connection point between the housing 32 and the metal sheath line 26.

Inside of the housing 32, the electrical connecting leads 22 are connected to connector pins 36 in an electrically conductive manner. A connection between the electrical connecting leads 22 and the connector pins 36 may be implemented, for example, through welding. But, in addition, still other common connecting techniques, for example, plugging, winding, soldering, etc. are possible.

The connector pins 36 are fixed in place in a base 38 comprised of an insulating material, for example, plastic. After having been connected to the electrical connecting leads 22, the connector pins 36, for example, may be cast in the base 38 in that an appropriate plastic material mass is filled in via an opening 40 of the housing 32. By way of fixing the position of the connector pins 36 in the base 38, an arrangement of the connector pins 36 in a specific reference grid is accomplished at the same time. As is shown in FIG. 2 by the plan view of the opening 40 of the connecting device 30 according to the line A—A in FIG. 1, altogether four connector pins 36 are arranged in the selected example on the corner points of a square. Of course, any other arrangement of the connector pins 36 that may be desired is possible if the prerequisite is met that the connector pins 36 are insertable into a corresponding counterplug device which will be explained below. With their free ends, the connector pins 36 project into the housing 32 so that, altogether, the connecting device 30 forms a connector coupling 44.

In the example shown, the housing 32 is essentially round, as is illustrated in FIG. 2. According to further embodiments, not shown, the housing 32 may also have any other geometric shape desired, for example, an oval shape, a rectangular shape, etc. Again, the prerequisite is that a corresponding counterplug corresponds with the shape of the housing 32 and the arrangement of the connector pins 36. At its end facing the opening 40, the housing 32 has a bead 48 and surrounding collar 46 which facilitates the insertion of a counterplug.

The base 38 may be provided with a through-opening 50 which connects an interior space of the metal sheath line 26 with an interior space of the housing 32. By way of this through-opening 50, of which optionally several may also be provided, a reference gas connection to the sensor element 12 is realized. Thus, a sensor element 12 which needs a gas reference for its operation, can also be used by way of the connecting device 30 which is fixedly connected to the metal sheath line 26. This means that, overall, the connecting device 30 can be used very flexibly for different types of sensor elements 12.

By way of the metal sheath line 26, which connects the sensor element 12 with the connecting device 30, a high-temperature resistant connection between the measuring point of the measuring instrument, the sensor element 12 and the interface to an evaluating circuit, the connecting device 30, is provided. It is not necessary to additionally provide any insulation elements, seals etc.

Furthermore, FIG. 1 shows a sectional view of a counterplug 52. The counterplug 52 is connected with electrical lines 54 which are, for example, a component part of a cable harness 56 that is fixedly installed in a motor vehicle. The counterplug 52 has a plug housing 58 whose outer contour is matched to the housing 32 of the connecting device 30. Here, the housing 32 as well as the plug housing 58 may be provided with means, for example, projections and corresponding recesses, not shown here, which only allow the plug housing 58 to be inserted into the housing 32 in a specific position.

Female contacts 60 are embedded, for example, latched, in the plug housing 58, with the connector pins 36 of the connecting device 30 being insertable into the female contacts. The female contacts 60 are connected to the lines 54 in an electrically conductive manner, for example, by way of crimping. Inside of the plug housing 58, recesses 62 are formed into which the lines 54 are guided and in which they are connected with the female contacts 60. For sealing purposes, the lines 54 are provided with a seal 64 which, on the one hand, effects a sealing of the connection point of the connector pins 36 with the female contacts 60 and, on the other hand, represents a strain relief for the lines 54. A further circumferential seal 66 is provided in the outer contour of the plug housing 58, ensuring that the plug housing 58 rests tightly against the housing 32.

Overall, the measuring instrument 10 comprising the sensor element 12, the protective device 24 and the connecting device 30 connected to the protective device 24 represents a compact and robust unit which complies with all requirements with regard to a reliable and continuous connection of the sensor element 12, even under extreme installation conditions, for example, in the engine compartment of a motor vehicle. A simplified assembly is possible by feeding the cable harness 56 to the measuring instrument 10 via a counterplug 52.

We claim:

1. An electrochemical measuring instrument for measurements at a measuring point which is removed from an evaluating circuit, comprising:

a sensor element having a housing and first electrical connecting leads for connecting the sensor element with the evaluating circuit, each of the electrical connecting leads having a first end remote from the sensor element;

a metal sheath, having one end fixedly connected to the housing of the sensor element and a second end facing away from the housing of the sensor element, and having an interior chamber through which the first electrical connecting leads are guided and protected against external influences; and an electrical plug connector, having a housing and electrical pins disposed within the housing and connected to the first ends of the electrical connecting leads, for electrically and detachably connecting the sensor element to a mating plug connector containing connector leads connected to the evaluating circuit, the housing of the electrical plug connector being fixedly connected to the metal sheath at the second end and, the electrical pins being molded in an insulating material base having at least one through-opening which connects the interior chamber of the metal sheath with the atmosphere or with a feed line connected to the atmosphere.

2. A measuring instrument according to claim 1 wherein the connector housing is molded to the metal sheath.

3. A measuring instrument according to claim 2 wherein the connector housing is of one piece unitary construction with the metal sheath.

4. A measuring instrument according to claim 1 wherein the connector housing is welded to the metal sheath line.

5. A measuring instrument according to claim 1 wherein the connector housing has means which force a correct pole connection of the connector pins.

6. A measuring instrument according to claim 1 wherein the sensor element is a solid electrolyte sensor.

7. A measuring instrument according to claim 6 wherein the sensor element is a lambda sensor.

* * * * *